United States Patent
Bera et al.

(10) Patent No.: US 10,358,363 B2
(45) Date of Patent: Jul. 23, 2019

(54) FLUORESCENT POLYMERS FOR WATER TREATMENT

(71) Applicant: Ecolab USA Inc., St. Paul, MN (US)

(72) Inventors: Tarun Kumar Bera, Pune (IN); Deepak Jadhav, Pune (IN); Kiran Phatangare, Ahmed Nagar (IN); Trishul Artham, Pune (IN); Jitendra Shah, Naperville, IL (US); Wesley Lamar Whipple, Naperville, IL (US); Winston Su, Naperville, IL (US); John David Morris, Naperville, IL (US); Paul Joseph Zinn, Naperville, IL (US)

(73) Assignee: Ecolab USA Inc., St. Paul, MN (US)

( * ) Notice: Subject to any disclaimer, the term of this patent is extended or adjusted under 35 U.S.C. 154(b) by 113 days.

(21) Appl. No.: 15/558,712

(22) PCT Filed: Mar. 17, 2016

(86) PCT No.: PCT/US2016/022811
§ 371 (c)(1),
(2) Date: Sep. 15, 2017

(87) PCT Pub. No.: WO2016/149471
PCT Pub. Date: Sep. 22, 2016

(65) Prior Publication Data
US 2018/0111858 A1    Apr. 26, 2018

(30) Foreign Application Priority Data
Mar. 17, 2015    (IN) ............................ 880/MUM/2015

(51) Int. Cl.
*C02F 1/56*    (2006.01)
*C07D 311/82*    (2006.01)
(Continued)

(52) U.S. Cl.
CPC ................ *C02F 1/56* (2013.01); *C02F 1/008* (2013.01); *C07D 311/82* (2013.01); *C09B 11/24* (2013.01); *C09B 69/103* (2013.01)

(58) Field of Classification Search
CPC ....... C02F 1/56; C07D 311/82; C09B 69/103; C09B 11/24
See application file for complete search history.

(56) References Cited

U.S. PATENT DOCUMENTS

| 5,705,394 A | 1/1998 | Ananthasubramanian et al. |
| 5,772,894 A | 6/1998 | Ward et al. |

(Continued)

FOREIGN PATENT DOCUMENTS

| CN | 105987982 A | 10/2016 |
| TW | 201348702 A | 12/2013 |

(Continued)

OTHER PUBLICATIONS

European Patent Office, Extended European Search Report in European Patent Application No. 16765728.7, 6 pp. (dated Jul. 31, 2018).

(Continued)

*Primary Examiner* — Catherine S Branch
(74) *Attorney, Agent, or Firm* — Leydig, Voit & Mayer, LTD.

(57) ABSTRACT

Novel fluorophores and their use as fluorescent tags for polymers used in wastewater treatment. The fluorophores are quaternary amine salts that can be used to synthesize fluorescent tagged polymers that are stable at varying pH, have significant water solubility, and may be fluorescent at wavelengths greater than 550 nm. The fluorophores readily undergo polymerization with vinylic monomers to form fluorescent tagged polymers with excellent incorporation of fluorophore into the polymer framework. The fluorescent (Continued)

tagged polymers are useful to monitor and optionally dose industrial wastewater.

20 Claims, 2 Drawing Sheets

(51) Int. Cl.
*C09B 69/10* (2006.01)
*C09B 11/24* (2006.01)
*C02F 1/00* (2006.01)

(56) References Cited

U.S. PATENT DOCUMENTS

| | | |
|---|---|---|
| 5,958,788 A | 9/1999 | Johnson et al. |
| 5,986,030 A | 11/1999 | Murray et al. |
| 2006/0160226 A1 | 7/2006 | Johnson |
| 2013/0233804 A1 | 9/2013 | Xie et al. |
| 2015/0041406 A1 | 2/2015 | Xie et al. |

FOREIGN PATENT DOCUMENTS

| | | |
|---|---|---|
| WO | WO 98/02492 A1 | 1/1998 |
| WO | WO 01/07430 A1 | 2/2001 |
| WO | WO 2016/133882 A1 | 8/2016 |
| WO | WO 2016/149471 A1 | 9/2016 |

OTHER PUBLICATIONS

Berger et al., "Transfer Constants to Monomer, Polymer, Catalyst, Solvent, and Additive in Free Radical Polymerization," Polymer Handbook, 3rd ed., John Wiley & Sons, New York, New York, pp. II/81-II/151.

Odian, "Radical Chain Polymerization: 3-6 Chain Transfer," *Principles of Polymerization*, 2nd ed., John Wiley & Sons, Inc., New York, New York, pp. 226-242 (1981).

Rybina et al., "Monitoring hydroquinone-quinone redox cycling by single molecule fluorescence spectroscopy," *Phys. Chem. Chem. Phys.*, vol. 16, pp. 19550-19555 (2014).

Israel Patent Office, International Search Report in International Patent Application No. PCT/US2016/022811, 3 pp. (dated May 29, 2016).

Israel Patent Office, Written Opinion in International Patent Application No. PCT/US2016/022811, 5 pp. (dated May 29, 2016).

FLUORESCENT POLYMERS FOR WATER TREATMENT

CROSS-REFERENCE TO RELATED APPLICATIONS

This application is a national stage application of International Patent Application Serial No. PCT/US2016/022811, filed Mar. 17, 2016 which claims priority to Indian Patent Application Serial No. 880/MUM/2015, filed on Mar. 17, 2015, each disclosure of which is incorporated herein by reference in its entirety.

FIELD OF INVENTION

The invention is directed to novel fluorescent compounds and their use as fluorescent tags in wastewater treatment processes. In particular, the invention is directed to the use of novel fluorophores and fluorescent tagged polymers for monitoring and optional dosage control of wastewater.

BACKGROUND OF THE INVENTION

Water treatment strategies commonly employ polymers for purification of industrial water systems. Fluorescent tagged polymers are often chosen as treatment chemicals because fluorescence can be used to monitor both concentration and location of the polymer or a substance associated with the polymer. A small quantity of fluorescent dye can be attached to the polymer and the fluorescence of the tagged polymer measured using conventional fluorescence detection equipment. Real time fluorescent methods can be used to rapidly adjust treatment dosage based on the measured performance of the water system. There are a number of fluorescent water treatment options available, but many existing treatment polymers and methods have certain disadvantages.

Wastewater can exhibit large background fluorescence due to the presence of naturally occurring organic and inorganic compounds, making it difficult to differentiate the fluorescent signal of the tagged polymer from the signal of the naturally occurring fluorescing particles in the wastewater. The fluorescence region of wastewater background is generally less than 550 nm, which overlaps with the fluorescence emission region of many commonly used fluorescent dyes. Thus, the development of a fluorescent tag and fluorescent tagged polymer that has a fluorescence emission range at a wavelength greater than 550 nm would be particularly beneficial.

However, the synthesis of fluorescent tagged polymers is commonly problematic because polymerization can occur with incomplete incorporation of fluorescent tag into the treatment polymer. Incorporation of the fluorescent monomer tag into the treatment polymer can be poor due to side reactions such as self polymerization and is often dependent upon the relative reactivity of the reaction monomers. Incomplete incorporation of the fluorescent tag into the treatment polymer can lead to additional chemical waste and polymer characterization challenges. Thus, there is a need for novel fluorescent monomers that will polymerize with high incorporation of the monomer into treatment polymers.

Moreover, fluorescence intensity of tagged polymers can vary if the polymer is susceptible to decomposition under certain pH conditions. For example, some polymers undergo cleavage of the fluorescent portion of the molecule due to acid- or base-catalyzed hydrolysis, resulting in unreliable fluorescence intensity measurements. Wastewater pH can vary based on the organic and inorganic substances present in the wastewater, which can range from highly acidic to highly basic. Thus, a fluorescent tag and fluorescent tagged polymer for wastewater treatment should have good stability under a range of pH conditions.

Accordingly, there is a need for improved fluorescent tags and improved fluorescent tagged polymers that can be used in tracing treatment chemicals in wastewater.

BRIEF SUMMARY OF THE INVENTION

In an embodiment, the invention provides a fluorophore of formula (I):

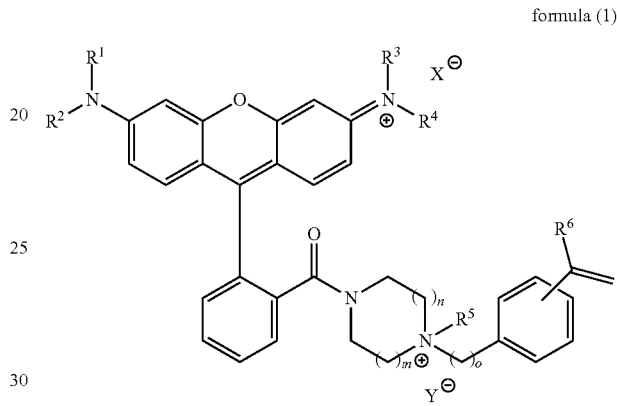

formula (1)

wherein $R^1$, $R^2$, $R^3$, and $R^4$ are independently selected from the group consisting of hydrogen, deuterium, $C_1$-$C_{12}$ alkyl, and aryl;

$R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl;

$R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl;

$X^-$ and $Y^-$ are independently selected anionic counterions, and are the same or different;

m and n are independently 1 or 2, and are the same or different; and o is 0, 1, 2, 3, 4, 5, or 6.

In another embodiment, the invention provides an improved fluorescent tagged polymer. The fluorescent tagged polymer comprises at least one vinylic monomer unit covalently bonded to a fluorophore of formula (I), wherein $R^1$, $R^2$, $R^3$, and $R^4$ are independently selected from the group consisting of hydrogen, deuterium, $C_1$-$C_{12}$ alkyl, and aryl; $R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl; $R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl; $X^-$ and $Y^-$ are independently selected anionic counterions, and are the same or different; m and n are independently 1 or 2, and are the same or different; and o is 0, 1, 2, 3, 4, 5, or 6.

In another embodiment, the invention provides a method of treating wastewater comprising dosing the wastewater with a treatment comprising at least one fluorescent tagged polymer to create treated wastewater, measuring fluorescence of the treated wastewater, and optionally adjusting dosing based on the measured fluorescence. The fluorescent tagged polymer comprises at least one vinylic monomer unit covalently bonded to a fluorophore of formula (I).

These and other features and advantages of the present invention will be apparent from the following detailed description, in conjunction with the appended claims.

DETAILED DESCRIPTION OF THE INVENTION

Figure 1:
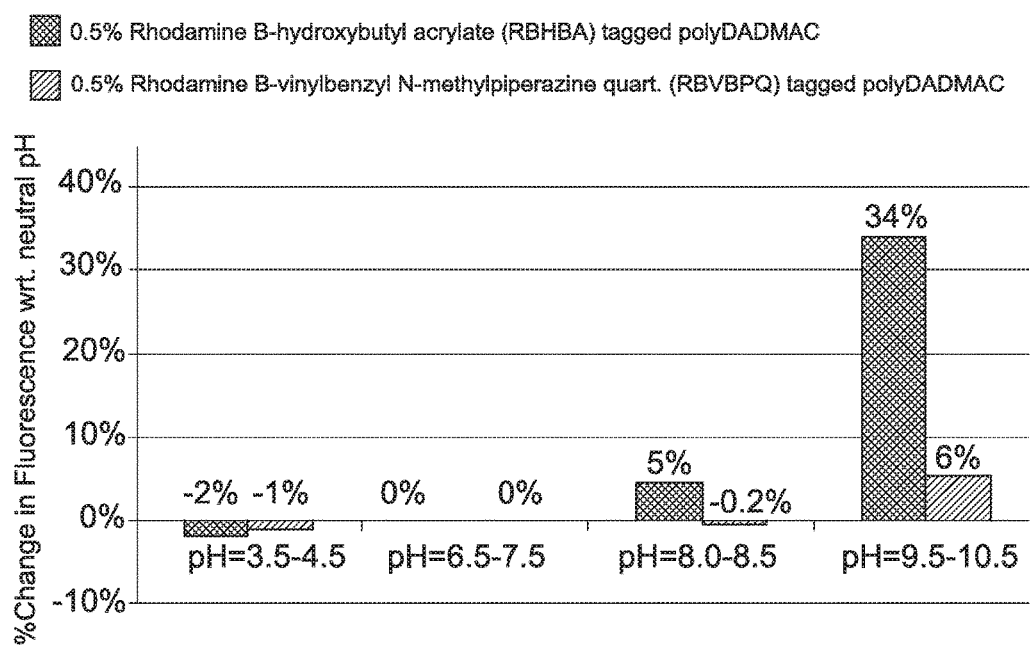
FIG. 1 is a bar graph which compares the pH dependent fluorescence of inventive Rhodamine B-vinylbenzyl 1-methylpiperamide quaternary salt (RBVBPQ) tagged polyDADMAC and Rhodamine B-hydroxybutylacrylate (RBHBA) tagged polyDADMAC.

The following definitions are provided to determine how terms used in this application, and in particular, how the claims are to be construed. The organization of the definitions is for convenience only and is not intended to limit any of the definitions to any particular category.

"Alkoxy" refers to a moiety of the formula RO—, where R is alkyl;

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like;

"Aryl" refers to a moiety of the formula Ar—, where Ar is an aromatic unit;

"Chain transfer agent" means any molecule, used in free-radical polymerization, which will react with a polymer radical forming a dead polymer and a new radical. In particular, adding a chain transfer agent to a polymerizing mixture results in a chain-breaking and a concomitant decrease in the size of the polymerizing chain. Thus, adding a chain transfer agent limits the molecular weight of the polymer being prepared;

"Cross-linking agent" or "branching agent" means a multifunctional monomer that when added to polymerizing monomer or monomers results in "branched" polymers or "cross-linked" polymers in which a branch or branches from one polymer molecule becomes attached to other polymer molecules;

"DADMAC" refers to diallyldimethylammonium chloride;

"Halogen" or "halo" refers to a moiety selected from the group consisting of F, Cl, Br, and I;

"Halosubstituted alkyl" refers to an alkyl group as described above substituted with one or more halogens, for example, chloromethyl, trifluoromethyl, 2,2,2-trichloroethyl, and the like;

"Heteroaryl" refers to a monocyclic or bicyclic 5- or 6-membered ring system as described herein, wherein the heteroaryl group is unsaturated and satisfies Hückel's rule. Non-limiting examples of suitable heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like;

"Incorporation percentage" refers to percentage of fluorophore reactant incorporated into the polymer during a polymerization reaction;

"Monitoring" means any type of tracing or tracking to determine the location or route of the polymers, and any type of determination of the concentration or amount of the polymer at any given site, including singular or intermittent or continuous monitoring;

"polyDADMAC" refers to poly(diallyldimethylammonium chloride);

"Structural modifier" means an agent that is added to the aqueous polymer solution to control the polymer structure and solubility characteristics. The structural modifier is selected from the group consisting of cross-linking agents and chain transfer agents;

"Vinyl" refers to a moiety which has a carbon-carbon double bond;

"Vinylbenzyl" refers to a moiety of the general formula

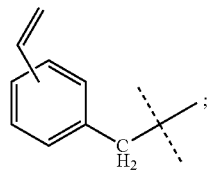

"Vinylic monomer" refers to a polymerizable allylic, vinylic, or acrylic compound. The vinylic monomer may be nonionic, anionic, or cationic;

"Wastewater" means water from a manufacturing process, municipal waste or other waters which are required to be treated prior to discharge to a receiving stream, lake, or other water way. Those having skill in the art will recognize that the disclosure refers to wastewater of any kind. Nonlimiting examples of wastewater include sewage, industrial waste, industrial cooling waters, industrial process waters, agricultural drainage, toxic waste, extreme pH waste, washing water, groundwater, cesspit leakage, human waste, septic tank water, storm drainage, seawater, river water, blackwater, and the like;

"Water soluble" means materials that are soluble in water to at least about 5%, by weight, at 25° C.

Whenever a range of the number of atoms in a structure is indicated (e.g., a $C_1$-$C_{12}$ alkyl, $C_2$-$C_{12}$ alkenyl, $C_2$-$C_{12}$ alkynyl, etc.), it is specifically contemplated that any sub-range or individual number of carbon atoms falling within the indicated range also can be used. Thus, for instance, the recitation of a range of 1-12 carbon atoms (e.g., $C_1$-$C_{12}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-12 carbon atoms (e.g., $C_2$-$C_{12}$) as used with respect to any chemical group (e.g., alkyl) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

Fluorescent compounds and methods are provided that can be used to treat wastewater. More particularly, a novel fluorophore is provided that can be used as a fluorescent tag for wastewater treatment polymers. The fluorescent tagged polymer can be used to monitor and optionally control dosage in wastewater. The fluorophores and fluorescent tagged polymers of the present invention are generally pH stable, which allows for utility in a variety of wastewater systems. In certain embodiments, the fluorescence emission wavelength of the fluorescent tagged polymer does not overlap with the background fluorescence emission wavelength of wastewater. The fluorophore can react with vinylic monomers selectively, forming a fluorescent tagged polymer with high incorporation of the fluorophore into the resulting polymer.

The fluorophores and fluorescent tagged compounds according to various embodiments of the present teachings can have the following components and features.

In an embodiment, the invention is directed to a fluorophore of formula (I):

formula (I)

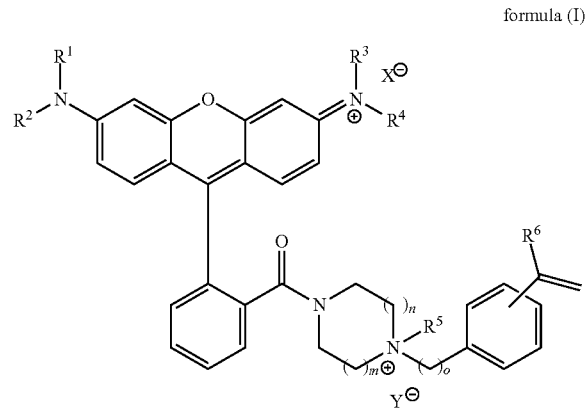

wherein $R^1$, $R^2$, $R^3$, and $R^4$ are independently selected from the group consisting of hydrogen, deuterium, $C_1$-$C_{12}$ alkyl, and aryl;

$R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl;

$R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl;

$X^-$ and $Y^-$ are independently selected anionic counterions, and can be the same or different;

m and n are independently 1 or 2, and can be the same or different; and o is 0, 1, 2, 3, 4, 5, or 6.

$X^-$ and $Y^-$ can be any suitable anionic counterion. Non-limiting examples of anionic counterions include chloride, bromide, iodide, fluoride, sulfate, perchlorate, acetate, trifluoroacetate, phosphate, nitrate, carbonate, bicarbonate, hydroxide, formate, chlorate, bromate, chlorite, thiosulfate, oxalate, cyanide, cyanate, tetrafluoroborate, hexafluorophosphate, hexafluoroantimonate, and the like.

The terminal olefin as shown can occupy any available position on the phenyl ring. Thus, in certain embodiments, the olefin can be at the ortho-, meta-, or para-position. In certain preferred embodiments, the terminal olefin is at the para-position.

In certain preferred embodiments, $R^1$, $R^2$, $R^3$, and $R^4$ are ethyl groups.

In certain preferred embodiments, $R^5$ is methyl.

In certain preferred embodiments, $X^-$ and $Y^-$ are both chloride.

In certain preferred embodiments, m and n are both 1.

In certain preferred embodiments, o is 1.

In a certain preferred embodiment, the fluorophore is

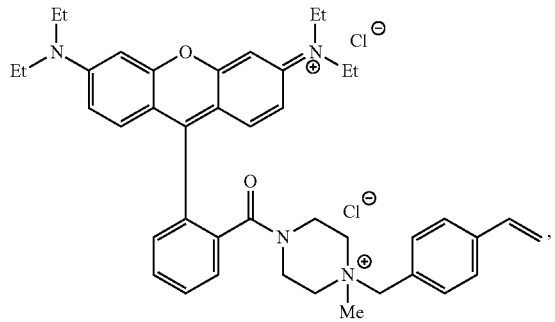

wherein Me is methyl and Et is ethyl.

The fluorophore of formula (I) can be prepared by any combination of suitable synthetic chemical methods. One method of preparation is a simple three-reaction synthesis using commercially available materials. Under air- and water-free conditions, Rhodamine B can react with any suitable chlorinating agent (e.g., thionyl chloride) to form a Rhodamine B acid chloride. Next, the Rhodamine B acid chloride undergoes amide formation with a suitable piperazine, diazepane, or diazocane. In certain preferred embodiments, the Rhodamine B acid chloride is reacted with an alkylpiperazine to form a Rhodamine B alkylpiperamide. The resulting Rhodamine B amide can be reacted with an alkylating agent to form a quaternary salt. For example, a Rhodamine B 1-alkylpiperamide reacts with a vinyl benzyl halide to form a Rhodamine B-vinylbenzyl 1-alkylpiperamide quaternary salt.

A fluorophore where o is 0 can be prepared by reacting the Rhodamine B acid chloride with a suitable vinylbenzylpiperazine, vinylbenzyldiazepane, or vinylbenzyldiazocane. The resulting Rhodamine B amide can be alkylated as discussed above.

An advantage of the present invention is that the fluorophore typically has fluorescence emission at a wavelength greater than about 550 nm, which is generally outside the spectral emission range of naturally-occurring wastewater compounds. Thus, the fluorophore can be used to synthesize fluorescent tagged polymers having a fluorescent signal that can be easily isolated from wastewater background signals, providing accurate quantification of the treatment polymer. While the fluorophore of formula (I) can have fluorescence emission at any wavelength, in certain preferred embodiments, the fluorophore has fluorescence emission at a wavelength of from about 550 nm to about 700 nm. Thus, in certain embodiments, the fluorophore has fluorescence emission at a wavelength of from about 550 nm to about 700 nm, from about 550 nm to about 675 nm, from about 550 nm to about 650 nm, from about 550 nm to about 625 nm, from about 550 nm to about 600 nm, from about 575 nm to about 700 nm, from about 575 nm to about 675 nm, from about 575 nm to about 650 nm, from about 575 nm to about 625 nm, from about 575 nm to about 600 nm, or from about 580 nm to about 600 nm.

Another advantage of the present invention is that the fluorophore of formula (I) can be highly water-soluble. In certain embodiments, the fluorophore of formula (I) can co-polymerize with a vinylic monomer with high incorporation of the fluorophore into the resulting polymer chain. While not wishing to be bound by any particular theory, it is believed that the enhanced incorporation of the fluorophore into the polymer chain is due in part to the high water solubility properties of the fluorophore. When soluble, it is believed that the fluorophore has increased proximity to the growing radical on the polymer chain. In certain embodiments, the fluorophore of formula (I) is soluble in water from about 80% to about >99% by weight, at 25° C. In other words, in certain embodiments, about 80% to about >99% of the fluorophore dissolves in water at 25° C. Thus, in certain embodiments, the fluorophore of formula (I) is soluble in water from about 80% to about >99%, from about 85% to about >99%, from about 90% to about >99%, from about 95% to about >99%, from about 98% to about >99%, or from about 99% to about >99% by weight, at 25° C. In certain embodiments, >99% of the fluorophore of formula (I) is soluble in water. While not wishing to be bound by any particular theory, it is believed that the high solubility is due to the high ionic character of the fluorophore.

In another embodiment, the invention is directed to a fluorescent tagged polymer comprising at least one vinylic monomer unit covalently bonded to a fluorophore of formula (I), wherein $R^1$, $R^2$, $R^3$, and $R^4$ are independently selected from the group consisting of hydrogen, deuterium, $C_1$-$C_{12}$ alkyl, and aryl; $R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl; $R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl; $X^-$ and $Y^-$ are independently selected anionic counterions, and can be the same or different; m and n are independently 1 or 2, and can be the same or different; and o is 0, 1, 2, 3, 4, 5, or 6.

The terminal olefin as shown can occupy any available position on the phenyl ring. Thus, in certain embodiments, the olefin can be at the ortho-, meta-, or para-position. In certain preferred embodiments, the terminal olefin is at the para-position.

The vinylic monomer may be nonionic, anionic, or cationic.

Representative non-ionic, water-soluble monomers include acrylamide, methacrylamide, N,N-dimethylacrylamide, N,N-diethylacrylamide, N-isopropylacrylamide, N-vinylformamide, N-vinylmethylacetamide, N-vinyl pyrrolidone, hydroxyethyl methacrylate, hydroxyethyl acrylate, hydroxypropyl acrylate, hydroxypropyl methacrylate, N-tert-butylacrylamide, N-methylolacrylamide, and the like.

Representative anionic monomers include acrylic acid, and its salts, including, but not limited to sodium acrylate, and ammonium acrylate, methacrylic acid, and its salts, including, but not limited to sodium methacrylate, and ammonium methacrylate, 2-acrylamido-2-methylpropanesulfonic acid, the sodium salt of AMPS, sodium vinyl sulfonate, styrene sulfonate, maleic acid, and its salts, including, but not limited to the sodium salt, and ammonium salt, sulfonate itaconate, sulfopropyl acrylate or methacrylate or other water-soluble forms of these or other polymerizable carboxylic or sulphonic acids. Sulfomethylated acrylamide, allyl sulfonate, sodium vinyl sulfonate, itaconic acid, acrylamidomethylbutanoic acid, fumaric acid, vinylphosphonic acid, vinylsulfonic acid, allylphosphonic acid, sulfomethylated acrylamide, phosphonomethylated acrylamide, and the like.

Representative cationic monomers include dialkylaminoalkyl acrylates and methacrylates and their quaternary or acid salts, including, but not limited to, dimethylaminoethyl acrylate methyl chloride quaternary salt, dimethylaminoethyl acrylate methyl sulfate quaternary salt, dimethylaminoethyl acrylate benzyl chloride quaternary salt, dimethylaminoethyl acrylate sulfuric acid salt, dimethylaminoethyl acrylate hydrochloric acid salt, dimethylaminoethyl methacrylate methyl chloride quaternary salt, dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, dialkylaminoalkylacrylamides or methacrylamides and their quaternary or acid salts such as acrylamidopropyltrimethylammonium chloride, dimethylaminoethyl acrylate methyl chloride quaternary salt, dimethylaminoethyl acrylate benzyl chloride quaternary salt, dimethylaminoethyl methacrylate methyl chloride quaternary salt, dimethylaminoethyl methacrylate benzyl chloride quaternary salt, methacrylarnidopropyl trimethylammonium chloride, dimethylaminopropyl acrylamide methyl sulfate quaternary salt, dimethylaminopropyl acrylamide sulfuric acid salt, dimethylaminopropyl acrylamide hydrochloric acid salt, methacrylamidopropyltrimethylammonium chloride, dimethylaminopropyl methacrylamide methyl sulfate quaternary salt, dimethylaminopropyl methacrylamide sulfuric acid salt, dimethylaminopropyl methacrylamide hydrochloric acid salt, diethylaminoethylacrylate, diethylaminoethylmethacrylate, diallyldiethylammonium chloride, diallyldimethylammonium chloride, and the like.

In certain preferred embodiments, the vinylic monomer is diallyldimethyl-ammonium chloride. Thus, in certain preferred embodiments, the fluorophore is used as a tag for monitoring and optionally dosing polyDADMAC.

The fluorescent tagged polymer can be a copolymer, terpolymer, quaterpolymer, and so on.

The fluorescent tagged polymer can be a linear polymer or a branched polymer. The fluorescent tagged polymer may be structurally-modified using a structural-modifier such as a cross-linking agent or a chain transfer agent.

Representative cross-linking agents include N,N-methylenebisacrylamide, N,N-methylenebismethacrylamide, triallylamine, triallyl ammonium salts, ethylene glycol dimethacrylate, diethylene glycol dimethacrylate, polyethylene glycol diacrylate, triethylene glycol dimethylacrylate, polyethylene glycol dimethacrylate, N-vinylacrylamide, N-methylallylacrylamide, glycidyl acrylate, acrolein, glyoxal and vinyltrialkoxysilanes such as vinyltrimethoxysilane (VTMS), vinyltriethoxysilane, vinyltris(β-methoxyethoxy)silane, vinyltriacetoxysilane, allyltrimethoxysilane, allyltriacetoxysilane, vinylmethyldimethoxysilane, vinyldimethoxyethoxysilane, vinylmethyldiacetoxysilane, vinyldimethylacetoxysilane, vinylisobutyldimethoxysilane, vinyltriisopropoxysilane, vinyltri-n-butoxysilane, vinyltrisecbutoxysilane, vinyltrihexyloxysilane, vinyltrimethoxysilane, vinylmethoxydihexyloxysilane, vinyldimethoxyoctyloxysilane, vinylmethoxydioctyloxysilane, vinyltrioctyloxysilane, vinylmethoxydilauryloxysilane, vinyldimethoxylauryloxysilane, vinylmethoxydioleyoxysilane, vinyldimethoxyoleyloxysilane, and the like.

Representative chain transfer agents include alcohols such as methanol, ethanol, 1-propanol, 2-propanol, butyl alcohol, and glycerol, and the like, sulfur compounds such as alkylthiols, thioureas, sulfites, and disulfides, carboxylic acids such as formic and malic acid, and their salts and phosphites such as sodium hypophosphite, and combinations thereof. See Berger et al., "Transfer Constants to Monomer, Polymer, Catalyst, Solvent, and Additive in Free Radical Polymerization," Section II, pp. 81-151, in "Polymer Handbook," edited by J. Brandrup and E. H Immergut, 3d edition, John Wiley & Sons, New York (1989) and George Odian, Principles of Polymerization, second edition, John Wiley & Sons, New York (1981).

In a certain preferred embodiment, the fluorescent tagged polymer comprises a unit represented by

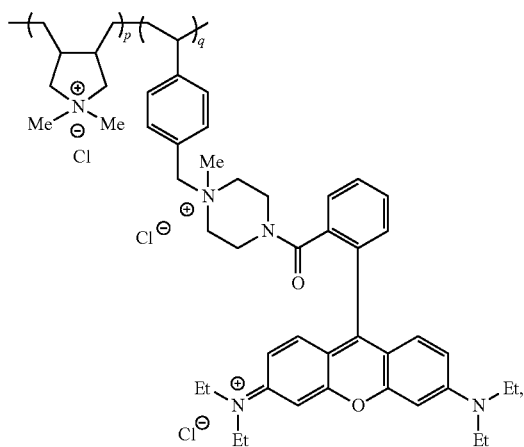

wherein Me is methyl and Et is ethyl.

In certain preferred embodiments, p is from about 95 to about 99.99 and q is from about 0.01 to about 5. In certain preferred embodiments, p is from about 99 to about 99.99 and q is from about 0.01 to about 1.

In certain embodiments, the fluorescent tagged polymer is essentially inert.

The fluorescent tagged polymer can be prepared by any suitable polymerization method. In certain embodiments, the fluorescent tagged polymer is synthesized using water-in-oil polymerization, dispersion polymerization, gel polymerization, or solution polymerization methods.

In a certain preferred embodiment, the fluorescent tagged polymer is prepared via free radical polymerization in an aqueous solution using a free radical initiator. In particular, a fluorophore of formula (I) undergoes free radical polymerization with one or more vinylic monomers in the presence of an azo-initiator. The polymerization reaction is generally carried out by intermittent addition of an azo-initiator, such as 2,2'-Azobis(2-methylpropionamidine)-dihydrochloride (i.e., V-50), to an aqueous solution comprising vinylic monomer and fluorophore at elevated temperature (e.g., 60° C.). The reaction vessel is purged with nitrogen throughout the polymerization reaction. After additional stirring at elevated temperature, the mixture is diluted and cooled to room temperature to terminate polymerization.

Another advantage of the present invention is that the fluorophore preferably undergoes polymerization with other vinylic monomers rather than self-polymerization. In general, the fluorophore of formula (I) can co-polymerize with a vinylic monomer with high incorporation of the fluorophore into the polymeric framework. Thus, in certain embodiments, the fluorophore of formula (I) co-polymerizes with one or more vinylic monomers with high incorporation of the fluorophore to form the corresponding fluorescent tagged polymer. In certain preferred embodiments, the fluorophore polymerizes with one or more vinylic monomers with an incorporation percentage of from about 90% to about >99%. Thus, in certain preferred embodiments, the fluorophore polymerizes with one or more vinylic monomers in an incorporation percentage of from about 90% to about >99%, from about 95% to about >99%, from about 96% to about >99%, from about 97% to about >99%, or from about 98% to about >99%.

Another advantage of the present invention is that the fluorescent tagged polymer generally has fluorescence emission at a wavelength greater than about 550 nm, which is generally outside the spectral emission range of naturally-occurring wastewater compounds. Thus, the fluorescent signal of the fluorescent tagged polymer can be easily isolated from wastewater background signals, providing more accurate quantification of the polymer treatment. While the fluorescent tagged polymers of the present invention can have fluorescence emission at any wavelength, in certain preferred embodiments, the fluorescent tagged polymer has fluorescence emission at a wavelength of from about 550 nm to about 700 nm. Thus, in certain preferred embodiments, the fluorescent tagged polymer has fluorescence emission at a wavelength of from about 550 nm to about 700 nm, from about 550 nm to about 675 nm, from about 550 nm to about 650 nm, from about 550 nm to about 625 nm, from about 550 nm to about 600 nm, from about 575 nm to about 700 nm, from about 575 nm to about 675 nm, from about 575 nm to about 650 nm, from about 575 nm to about 625 nm, from about 575 nm to about 600 nm, or from about 580 nm to about 600 nm.

Another advantage of the present invention is that the fluorescent tagged polymer generally has good stability over a wide pH range. The stability of fluorescent tagged polymers is generally a function of time, temperature, and pH. In contrast to many fluorescent polymers, the fluorescent tagged polymer of the present invention has remarkable stability under basic conditions, including at pH levels greater than 9. In certain preferred embodiments, the fluorescence intensity of the fluorescent tagged polymer is independent of pH conditions. As a result, the fluorescent tagged polymer can be used to treat wastewater from a variety of sources. Without wishing to be bound by any particular theory, it is believed that the amide moiety of the polymer has increased resistance to hydrolysis under both acidic and basic conditions, rendering the fluorescent tagged polymer stable under these conditions. Higher structural stability allows for more accurate quantification of the fluorescent tagged polymer.

In certain embodiments, the fluorescent tagged polymer in an aqueous solution having a pH of from about 2 to about 11 has a fluorescence intensity variance of less than about 6%. In certain embodiments, the fluorescent tagged polymer has a fluorescence intensity variance of less than about 1% when in an aqueous solution having a pH of from about 2 to about 9. Thus, in certain embodiments, the fluorescent tagged polymer has a fluorescence intensity variance of less than about 1% when in an aqueous solution having a pH of from about 2 to about 9, from about 2 to about 8, from about 2 to about 7, from about 2 to about 6, from about 2 to about 5, from about 3 to about 9, from about 3 to about 8, from about 3 to about 7, from about 3 to about 6, from about 4 to about 9, from about 4 to about 8, from about 4 to about 7, from about 4 to about 10, from about 5 to about 9, from about 5 to about 8, from about 7 to about 10, or from about 8 to about 10.

Another advantage of the present invention is that the fluorescent tagged polymer has enhanced water solubility. In certain embodiments, the fluorescent tagged polymers of the present invention are highly water-soluble. In certain preferred embodiments, the fluorescent tagged polymer of the present invention is soluble in water from about 80% to about >99% by weight, at 25° C. In other words, in certain embodiments, about 80% to about >99% of the fluorescent tagged polymer dissolves in water at 25° C. Thus, in certain preferred embodiments, the fluorescent tagged polymer is soluble in water from about 80% to about >99%, from about 85% to about >99%, from about 90% to about >99%, from about 95% to about >99%, or from about 98% to about >99%, at 25° C. In certain embodiments, >99% of the fluorescent tagged polymer is soluble in water.

The fluorescent tagged polymer can comprise fluorophore in any suitable amount. In certain preferred embodiments, the fluorescent tagged polymer comprises fluorophore in an amount of from about 0.01 wt % to about 5 wt %, based on the weight of fluorescent tagged polymer. Thus, in certain preferred embodiments, the fluorescent tagged polymer comprises fluorophore of formula (I) in an amount of from about 0.01 wt % to about 5 wt %, from about 0.01 wt % to about 4 wt %, from about 0.01 wt % to about 3 wt %, from about 0.01 wt % to about 2 wt %, from about 0.01 wt % to about 1 wt %, from about 0.01 wt % to about 0.5 wt %, from about 0.01 wt % to about 0.1 wt %, from about 0.1 wt % to about 5 wt %, from about 0.1 wt % to about 4 wt %, from about 0.1 wt % to about 3 wt %, from about 0.1 wt % to about 2 wt %, from about 0.1 wt % to about 1 wt %, from about 0.5 wt % to about 5 wt %, from about 0.5 wt % to about 4 wt %, from about 0.5 wt % to about 3 wt %, from about 0.5 wt % to about 2 wt %, from about 0.5 wt % to about 1 wt %, or from about 1 wt % to about 5 wt %, based on the weight of the fluorescent tagged polymer.

The molecular weight of the fluorescent tagged polymer is not limited. In certain preferred embodiments, the fluorescent tagged polymer has a molecular weight of from about 550 Daltons to about 50 million Daltons. For example, the fluorophore of the present invention may be used to monitor and optionally dose DADMAC polymers, which typically have a molecular weight of from about 10,000 Daltons to about 1,000,000 Daltons. Moreover, the fluorophores of the present invention may be used to monitor and optionally dose polyacrylamide flocculants, which typically can have a molecular weight in the range of from about 1 million Daltons to about 40 million Daltons. In certain preferred embodiments, the fluorescent tagged polymer has a molecular weight of from about 550 Daltons to about 50 million Daltons, from about 1,000 Daltons to about 50 million Daltons, from about 10,000 Daltons to about 50 million Daltons, from about 100,000 Daltons to about 50 million Daltons, from about 550 Daltons to about 10,000,000 Daltons, from about 1,000 Daltons to about 10,000,000 Daltons, from about 10,000 Daltons to about 10,000,000 Daltons, from about 100,000 Daltons to about 10,000,000 Daltons, from about 1,000,000 Daltons to about 10,000,000 Daltons, from about 550 Daltons to about 1,000,000 Daltons, from about 1,000 Daltons to about 1,000,000 Daltons, from about 10,000 Daltons to about 1,000,000 Daltons, from about 100,000 Daltons to about 1,000,000 Daltons, from about 1,000 Daltons to about 100,000 Daltons, from about 10,000 Daltons to about 100,000 Daltons, from about 550 Daltons to about 50,000 Daltons, from about 1,000 Daltons to about 50,000 Daltons, or from about 10,000 Daltons to about 50,000 Daltons.

The fluorescence emission of the fluorescent tagged polymer can be used to determine the amount of the fluorescent tagged polymer present in wastewater. In an embodiment, the invention provides a method of treating wastewater comprising dosing the wastewater with a treatment comprising at least one fluorescent tagged polymer to create treated wastewater, wherein the at least one fluorescent tagged polymer comprises at least one vinylic monomer unit covalently bonded to a fluorophore of formula (I), wherein $R^1$, $R^2$, $R^3$, and $R^4$ are independently selected from the group consisting of hydrogen, deuterium, $C_1$-$C_{12}$ alkyl, and aryl; $R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl; $R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl; $X^-$ and $Y^-$ are independently selected anionic counterions, and can be the same or different; m and n are independently 1 or 2, and can be the same or different; o is 0, 1, 2, 3, 4, 5, or 6. The fluorescence of the treated wastewater is measured and the dosing is optionally adjusted based on the measured fluorescence. Automated dosage control of the fluorescent tagged polymer in wastewater can be achieved via on-line fluorescence measurement.

Fluorometric analysis can be conducted using a light source and a fluorescence detector (e.g., fluorometer) configured to fluorometrically detect fluorescence as known in the art. In a certain preferred embodiment, the fluorometric techniques are carried out using a light source capable of shining light at a particular wavelength, or range thereof, into an aqueous liquid that has been treated with a fluorescent tagged polymer of the present invention.

The invention provides the ability to monitor and control the dosage of coagulants and/or flocculants online and in real time using TRASAR or 3D TRASAR technology, or a similar technology. The ability to automate such treatment can improve the efficiency and reduce total cost of operation of raw water and/or industrial wastewater treatment systems. The invention at hand can be used to improve effluent quality for regulatory compliance and system stability. The invention can also allow for more accurate chemical dosing for performance optimization and alarms on system issues, such as pump failures and empty chemical tanks, thereby reducing system upsets. The invention can be used in various wastewater automation processes, such as dissolved air flotation ("DAF") automation and clarification dosage optimization.

The fluorescent tagged polymer can be used as an effective treatment for wastewater having fluorescence at any wavelength. In certain embodiments, the invention overcomes issues related to signal interference (i.e., overlap of treatment polymer fluorescence and wastewater background fluorescence). Wastewater is generally fluorescent at a wavelength less than about 550 nm. In certain embodiments, the fluorescent tagged polymer of the present invention has fluorescence emission at a wavelength greater than about 550 nm. Thus, in certain embodiments, the fluorescent tagged polymer has a fluorescence wavelength that does not overlap with the fluorescence wavelength of wastewater.

The fluorescent tagged polymer can be used as an effective treatment for wastewater having any pH. In certain preferred embodiments, the fluorescent tagged polymer is added to wastewater having a pH of from about 2 to about 11. Thus, in certain preferred embodiments, the fluorescent tagged polymer is added to wastewater having a pH of from about 2 to about 11, from about 2 to about 10, from about 2 to about 9, from about 2 to about 8, from about 2 to about 7, from about 2 to about 6, from about 2 to about 5, from about 4 to about 11, from about 5 to about 11, from about 6 to about 11, from about 7 to about 11, from about 8 to about 11, from about 8 to about 10, from about 3 to about 10, from about 4 to about 10, from about 4 to about 8, or from about 5 to about 8. In certain embodiments, the fluorescent tagged polymer has exemplary performance in a basic wastewater composition. A typical basic wastewater composition can have a pH of from about 9 to about 11.

While fluorescent tagged polymer can be added to wastewater at any dosage rate, the inventive fluorescent tagged polymer is generally most effective at a dosage rate of from about 0.01 ppm to about 1,000 ppm. In certain embodiments, the fluorescent tagged polymer is added to wastewater at a dosage rate of from about 0.01 ppm to about 500 ppm. In certain preferred embodiments, the fluorescent tagged polymer is added to wastewater at a dosage rate of from about 0.01 ppm to about 100 ppm. Thus, in certain preferred embodiments, the fluorescent tagged polymer is added to wastewater at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

Those skilled in the art will appreciate that the fluorescent tagged polymer treatment comprising a fluorophore of formula (I) may be added to wastewater alone or in combination with other treatment chemicals and/or polymers, including untagged polymers. Multiple treatment chemicals can be dosed as a combined treatment or each treatment chemical can be added separately. For example, the fluorescent tagged polymer may be added to wastewater in combination with a variety of additional additives, such as anti-microbial agents, anti-scaling agents, anti-corrosion agents, colorants, fillers, buffers, surfactants, viscosity modifiers, chelating agents, masking agents, oxygen scavengers, and indicator dyes. The fluorescent tagged polymer or composition comprising fluorescent tagged polymer can be added in any form. In certain embodiments, the fluorescent tagged polymer or composition comprising fluorescent tagged polymer can be added to wastewater as a solution or as a dried solid.

In certain embodiments, the fluorescent tagged polymer comprising a fluorophore of formula (I) can be used as a treatment polymer in a method of monitoring turbidity of wastewater and optionally adjusting dosage of the treatment polymer based on the measured turbidity. In particular, the invention is directed to a method of treating wastewater comprising dosing the wastewater with a treatment polymer comprising at least one fluorescent tagged polymer to create treated wastewater, measuring the turbidity of wastewater, and optionally adjusting dosage of the treatment based on the measured turbidity. The fluorescent tagged polymer comprises at least one vinylic monomer unit covalently bonded to a fluorophore of formula (I).

In certain embodiments, the fluorescent tagged polymer is capable of lowering the turbidity of wastewater when present in wastewater having a turbidity of from about 1 NTU to about 20,000 NTU. Thus, in certain embodiments, the fluorescent tagged polymer is added to wastewater having a turbidity of from about 1 NTU to about 20,000 NTU, from about 1 NTU to about 10,000 NTU, from about 1 NTU to about 5,000 NTU, from about 1 NTU to about 1,000 NTU, from about 1 NTU to about 500 NTU, or from about 1 NTU to about 100 NTU. In certain embodiments, the fluorescent tagged polymer is capable of lowering the turbidity of wastewater by at least about 50%. In certain embodiments, the fluorescent tagged polymer is capable of lowering the turbidity of wastewater by at least about 75%. In certain embodiments, the fluorescent tagged polymer is capable of lowering the turbidity of wastewater by at least about 95%.

The following examples further illustrate the invention but, of course, should not be construed as in any way limiting its scope.

EXAMPLE 1

This Example demonstrates a method of synthesis of a fluorophore in accordance with an embodiment of the invention.

General Chemistry Methods. All air or moisture sensitive reactions were performed under positive pressure of nitrogen with oven-dried glassware. Anhydrous dichloromethane and ethyl acetate were purchased from Merck & Co. Anhydrous N,N-dimethylformamide (DMF) and triethylamine were purchased from Sigma-Aldrich (St. Louis, Mo.). Neutral alumina was purchased from Merck Specialties Pvt. Ltd. HPLC analysis was performed on a Dionex UltiMate UHPLC 3000. The column used was an Agilent TC-C18 4.6×250 mm (5 µm particle size) at a flow rate of 1 mL/min. The mobile phase was acetonitrile (10%) in water (Solvent A) or pure acetonitrile (Solvent B) (each containing 0.1% acetic acid).

Step 1. A solution of Rhodamine B (4.1 mmol, 2.0 g) in dichloromethane (80 mL) was treated with triethylamine (4.1 mmol, 0.57 mL) at room temperature. The mixture was cooled to 0° C. and treated dropwise with thionyl chloride (12.3 mmol, 0.9 mL). The resulting reaction mixture was stirred under refluxed for 1.5 hours, cooled to 0° C., and treated dropwise with N-methylpiperazine (16.4 mmol, 1.81 mL). The reaction mixture was allowed to warm to room temperature and then refluxed for 1.5 hours. The solvent was evaporated in vacuo, the residue was washed with 1% methanol in ethyl acetate (15 mL×3), and dried under vacuum to obtain the crude amide (4.3 g). The crude amide was purified on a neutral alumina column using 10-15% methanol in ethyl acetate and dried in vacuo to give the title compound as a brown colored solid.

N-(6-(diethylamino)-9-(2-(4-methylpiperazine-1-carbonyl)phenyl)-3H-xanthen-3-ylidene)-N-ethylethanaminium chloride

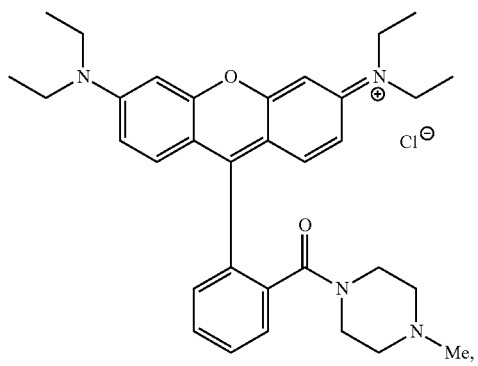

wherein Me is methyl.

Step 2. The amide (2.3 mmol, 1.3 g) from step 1 was dissolved in DMF (10 mL) and treated with 4-vinylbenzyl chloride (16.8 mmol, 2.4 mL) at room temperature. The reaction mixture was stirred at room temperature for 2 days. The crude product was purified on a neutral alumina column using 10-15% methanol in ethyl acetate and dried in vacuo to give the product as a dark green crystalline solid (0.98 g, 95% pure by HPLC).

Rhodamine B-Vinylbenzyl-1-Methylpiperamide Quaternary Salt (RBVBPQ)

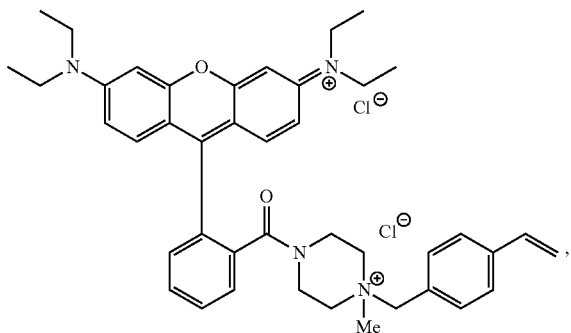

wherein Me is methyl.

EXAMPLE 2

This Example demonstrates a method of synthesizing a fluorescent tagged polymer in accordance with an embodiment of the invention.

General Analytical Methods. The weight-average molecular weight of polymers was determined by a size exclusion chromatography (SEC) coupled with a multi-angle-laser-light-scattering detector (Wyatt HELEOS-II) and a differential refractometer (Wyatt Optilab rEX). The percentage of dye incorporation was determined by size exclusion chromatography coupled with a fluorometer (Waters 474 Scanning Fluorescence Detector). Specifically, it was calculated based on the fluorescence intensity of polymer peak in SEC chromatogram, and the total fluorescence obtained in flow injection analysis without SEC columns.

Diallyldimethylammonium chloride (DADMAC, 60 wt %, 80 g) and RBVBPQ (280 mg) were mixed in water under nitrogen. The reaction mixture was treated with sodium chloride (18 g) and heated to 60° C. while under stirring. The reaction mixture was charged with 1 mL of 0.37 M aq. solution of 2,2'-azobis(2-methylpropionamidine)dihydrochloride solution (i.e., V-50) every two hours. The reaction temperature was maintained at 60° C. After 8 hours, the polymer mixture was diluted with water and the reaction was stirred at 60° C. overnight. After 13 hours, a final portion of V-50 (1 mL of 0.37 M aq.) was added (same amount as above aliquots) and the polymer mixture was stirred. The polymerization was terminated by adding distilled water and removing the polymer mixture from heat. After 30 minutes, the reaction was charged with additional water and stirred for a few minutes to give the RBVBPQ tagged polyDADMAC as a solution. The polymer had a viscosity of 1360-1370 cP (as measured using a Brookfield Viscometer Spindle no 31, 25° C., 20 RPM). The percentage of tag incorporated into the polymer (i.e., % dye incorporation) was 93%.

RBVBPQ Tagged polyDADMAC

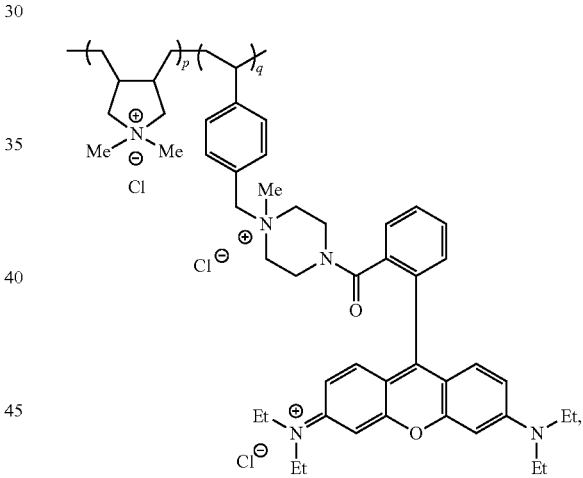

wherein Me is methyl and Et is ethyl.

EXAMPLE 3

This Example demonstrates the dependence of fluorescence intensity on pH for a fluorescent tagged polymer in accordance with an embodiment of the invention and a Rhodamine B ester derivative.

For the experiment, RBVBPQ tagged polyDADMAC and Rhodamine B-hydroxybutyl acrylate (RBHBA) tagged polyDADMAC were used to prepare aqueous solutions having different pH values. The solutions were analyzed to determine the fluorescence variation. The fluorescence variation is defined as the difference between the fluorescence intensity of a substance at a specific pH and the fluorescence intensity of a substance at neutral pH (about 7), divided by the initial fluorescence intensity, and multiplied by 100.

RBHBA Tagged polyDADMAC

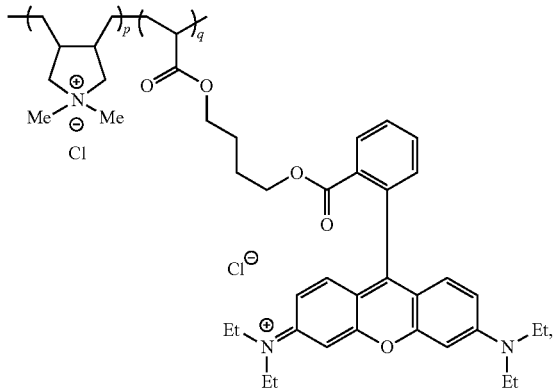

wherein Me is methyl and Et is ethyl.

Accordingly, each fluorescent tagged DADMAC polymer (each comprising 0.5 wt % of corresponding fluorophore) was individually diluted with deionized water to prepare a stock solution. Each stock solution was used to prepare three additional solutions (solutions A-C) having pH levels of about 4 (solution A), about 8 (solution B), and about 10 (solution C). To form solutions A-C, the pH of the stock solution was adjusted from neutral to the target pH by adding NaOH and HCl as necessary. Fluorometric analysis was performed on a FluoroMax-4 Fluorescence Spectrophotometer from HORIBA Scientific using a fluorescence excitation and emission slit width of 5 nm. The solutions were subjected to a fluorescence excitation wavelength of 550 nm and screened in the range of 570 nm to 700 nm. An average fluorescence emission wavelength of 581 nm to 591 nm was used to examine the fluorescence intensity of solutions A-C. The fluorescence variation was found for each sample.

The fluorescence variation of each polymer was added to the bar graph shown in FIG. 1. As shown in FIG. 1, at a pH of about 4, the RBVBPQ tagged polyDADMAC solution has a fluorescence variation of −1%, while the RBHBA tagged polyDADMAC solution has a fluorescence variation of −2%. At a pH of about 8, the RBVBPQ tagged polyDADMAC solution has a negligible fluorescence variation, while the RBHBA tagged polyDADMAC has a fluorescence variation of 5%. At a pH of about 10, the RBVBPQ tagged polyDADMAC solution has a fluorescence variation of 6%, while the RBHBA tagged polyDADMAC solution has a fluorescence variation of 34%. The inventive fluorescent tagged polymer (RBVBPQ tagged polyDADMAC) has a lower fluorescence variation than the Rhodamine B ester (RBHBA tagged polyDADMAC) over a range of pH levels. Without wishing to be bound by a particular theory, it is believed that the higher structural stability of the inventive fluorescent tagged polymer (RBVBPQ tagged polyDADMAC) is responsible for the low fluorescence variation of the polymer.

This Example demonstrates that a fluorescent tagged polymer of an embodiment of the invention (RBVBPQ tagged polyDADMAC) has low pH sensitivity.

EXAMPLE 4

This Example demonstrates the wastewater treatment performance of a fluorescent tagged polymer in accordance with an embodiment of the invention.

For the experiment, wastewater was dosed with varying amount of fluorescent tagged polymer and analyzed to determine the effect of dosage on turbidity and fluorescence intensity.

Accordingly, chemical industry wastewater having a pH of about 8 was dosed with RBVBPQ tagged polyDADMAC (comprising 0.5 wt % fluorophore) at dosages between 30-150 ppm. The wastewater/polymer mixtures were mixed at 250 RPM for 1.5 minutes in a laboratory Jar Tester (Phipps and Bird Programmable Jar Tester). Anionic flocculant was dosed to each Jar Tester and mixed at 250 RPM for 30 seconds. The mixing speed was decreased to 50 RPM and mixing continued for an additional 1 minute. The mixture was allowed to settle for 15 minutes and the supernatant was collected.

The supernatant was analyzed for both turbidity and fluorescence. Fluorometric analysis was performed on a FluoroMax-4 Fluorescence Spectrophotometer from HORIBA Scientific using a fluorescence excitation and emission slit width of 5 nm. The samples were subjected to a fluorescence excitation wavelength of 550 nm. Fluorescence of the treated water was screened at a fluorescence excitation range of 570 nm to 700 nm. An average fluorescence emission wavelength of 581 nm to 591 nm was used to examine the fluorescence intensity of the treated water.

Figure 2:
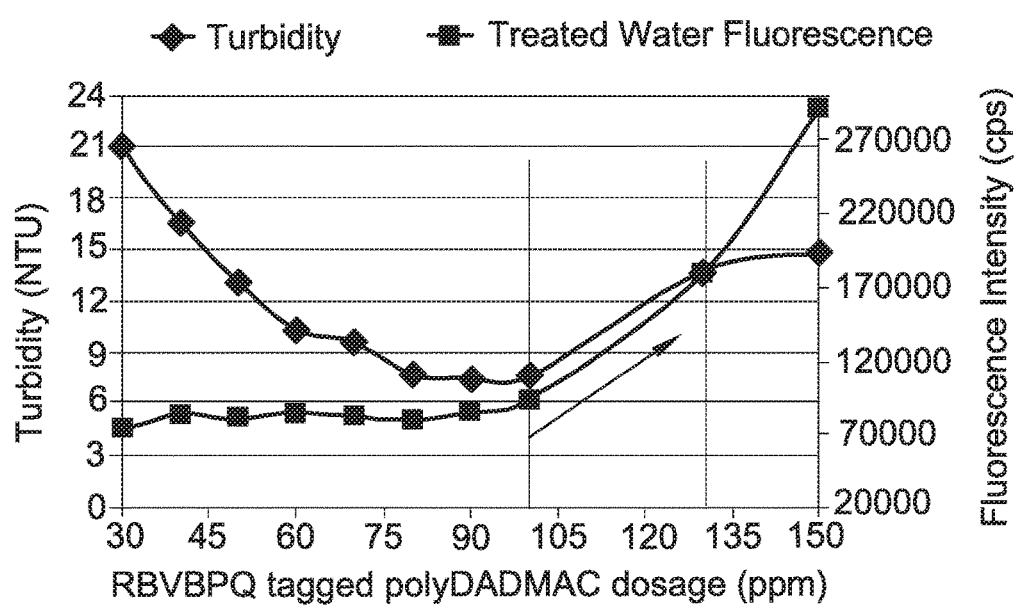
FIG. 2 is a line graph that illustrates the utility of inventive RBVBPQ tagged polyDADMAC for wastewater treatment.

The wastewater turbidity and fluorescence data were plotted on the graph shown in FIG. 2. As shown in FIG. 2, the RBVBPQ tagged polyDADMAC lowered the turbidity of the wastewater when used at a dosage of up to 100 ppm. The treated water turbidity measurement suggests that the optimum dosage is in the range of 80 to 100 ppm. The treated water fluorescence measurement showed a flat line until optimum dosage was reached, then a sharp increase in fluorescence beyond a dosage of 100 ppm.

This Example demonstrates that treated water fluorescence monitoring with a fluorescent tagged polymer of an embodiment of the invention can be used for dosage control and automation of wastewater treatment products.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A fluorophore of formula (I):

formula (I)

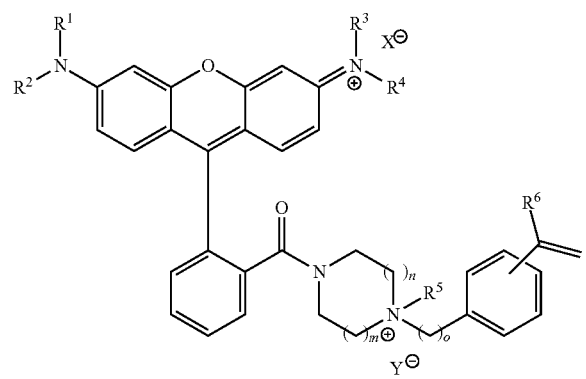

wherein $R^1$, $R^2$, $R^3$, and $R^4$ are independently selected from the group consisting of hydrogen, deuterium, $C_1$-$C_{12}$ alkyl, and aryl;

$R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl;

$R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl;

$X^-$ and $Y^-$ are independently selected anionic counterions;

m and n are independently 1 or 2; and o is 0, 1, 2, 3, 4, 5, or 6.

2. The fluorophore of claim 1, wherein in and n are 1.

3. The fluorophore of claim 1, wherein $R^5$ is methyl.

4. The fluorophore of claim 1, wherein the fluorophore is

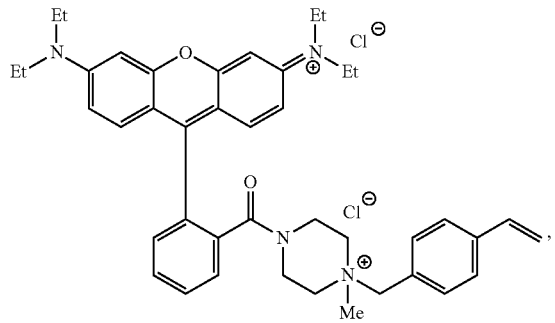

wherein Me is methyl and Et is ethyl.

5. The fluorophore of claim 1, wherein the fluorophore has fluorescence emission at a wavelength of from about 550 nm to about 700 nm.

6. A fluorescent tagged polymer comprising at least one vinylic monomer unit covalently bonded to a fluorophore of formula (I):

formula (I)

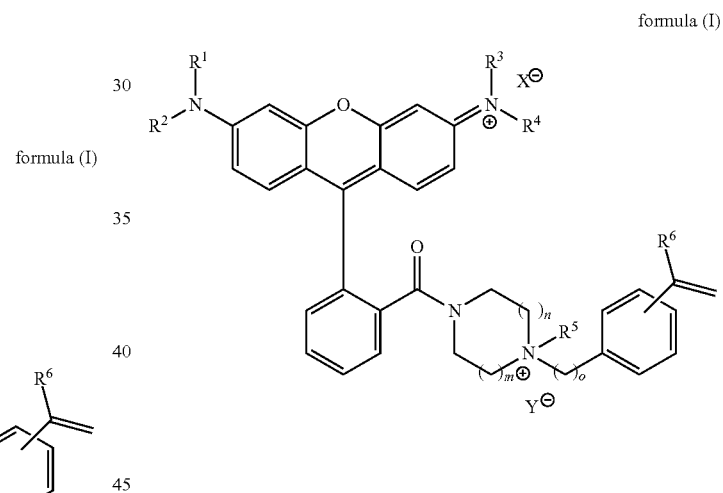

wherein $R^1$, $R^2$, $R^3$, and $R^4$ are independently selected from the group consisting of hydrogen, deuterium, $C_1$-$C_{12}$ alkyl, and aryl;

$R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl;

$R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl;

$X^-$ and $Y^-$ are independently selected anionic counterions;

m and n are independently 1 or 2; and o is 0, 1, 2, 3, 4, 5, or 6.

7. The fluorescent tagged polymer of claim 6, wherein m and n are 1.

8. The fluorescent tagged polymer of claim 6, wherein the fluorophore is

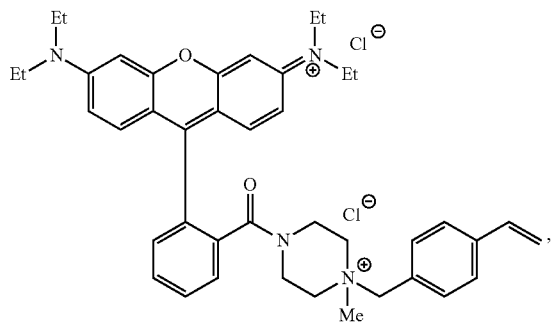

wherein Me is methyl and Et is ethyl.

9. The fluorescent tagged polymer of claim 6, wherein the vinylic monomer is a cationic monomer.

10. The fluorescent tagged polymer of claim 9, wherein the vinylic monomer is diallyldimethylammonium chloride.

11. The fluorescent tagged polymer of claim 6, wherein the fluorescent tagged polymer is branched or crosslinked.

12. The fluorescent tagged polymer of claim 6, wherein the fluorescent tagged polymer has a molecular weight of from about 1,000 Daltons to about 10,000,000 Daltons.

13. The fluorescent tagged polymer of claim 6, wherein the fluorophore is in an amount of from about 0.01% to about 2% by weight based on the weight of the fluorescent tagged polymer.

14. The fluorescent tagged polymer of claim 6, wherein the fluorescent tagged polymer has fluorescence emission at a wavelength of from about 550 nm to about 700 nm.

15. The fluorescent tagged polymer of claim 6, wherein the fluorescent tagged polymer comprises a unit represented by

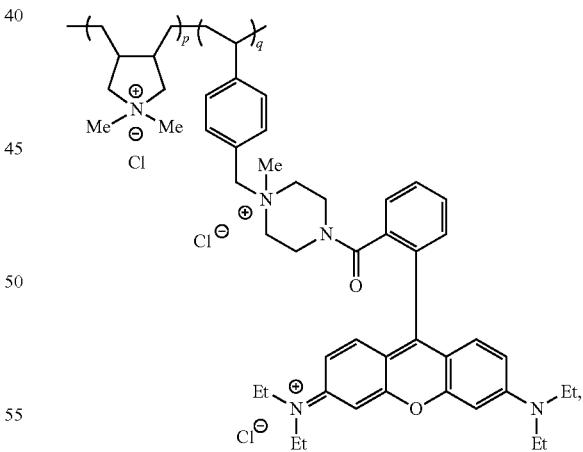

wherein Me is methyl, Et is ethyl, p is from about 95 to about 99.99, and q is from about 0.01 to about 5.

16. The fluorescent tagged polymer of claim 15, wherein p is from about 99 to about 99.99 and q is from about 0.01 to about 1.

17. A method of treating wastewater comprising:
dosing the wastewater with a treatment comprising at least one fluorescent tagged polymer to create treated wastewater, wherein the at least one fluorescent tagged polymer comprises at least one vinylic monomer unit covalently bonded to a fluorophore of formula (I)

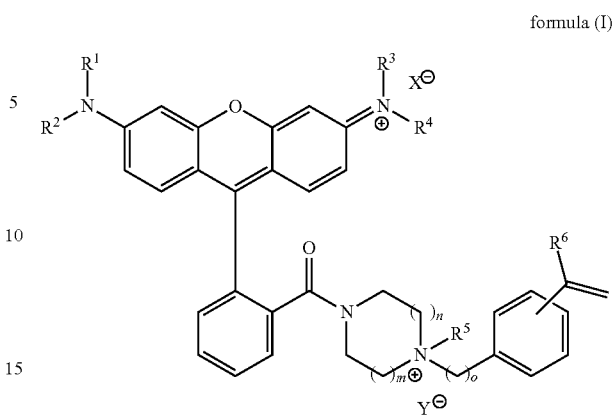

formula (I)

wherein $R^1$, $R^2$, $R^3$, and $R^4$ are independently selected from the group consisting of hydrogen, deuterium, $C_1$-$C_{12}$ alkyl, and aryl;

$R^5$ is selected from the group consisting of hydrogen, deuterium, $C_1$-$C_{12}$ alkyl, $C_2$-$C_{12}$ alkenyl, $C_2$-$C_{12}$ alkynyl, aryl, heteroaryl, and halosubstituted alkyl;

$R^6$ is selected from the group consisting of hydrogen, $C_1$-$C_{12}$ alkyl, $C_2$-$C_{12}$ alkenyl, aryl, heteroaryl, halo, halosubstituted alkyl, cyano, nitro, alkoxy, carboxyl, and sulfonyl;

$X^-$ and $Y^-$ are independently selected anionic counterions;

m and n are independently 1 or 2, and are the same or different;

o is 0, 1, 2, 3, 4, 5, or 6;

measuring fluorescence of the treated wastewater; and optionally adjusting dosing based on the measured fluorescence.

18. The method of claim 17, wherein the fluorescent tagged polymer comprises a unit represented by wherein Me is methyl, Et is ethyl, p is from about 95 to about 99.99, and q is from about 0.01 to about 5.

19. The method of claim 17, wherein the fluorescent tagged polymer is present in the wastewater at a dosage of from about 0.01 ppm to about 100 ppm.

20. The method of claim 17, wherein the wastewater has a pH of about 8 to about 11.

* * * * *

UNITED STATES PATENT AND TRADEMARK OFFICE
CERTIFICATE OF CORRECTION

PATENT NO. : 10,358,363 B2
APPLICATION NO. : 15/558712
DATED : July 23, 2019
INVENTOR(S) : Tarun Kumar Bera et al.

Page 1 of 1

It is certified that error appears in the above-identified patent and that said Letters Patent is hereby corrected as shown below:

In the Specification

At Column 1, Line 9, delete "2016" and insert --2016,--

In the Claims

At Column 19, Claim 1, Lines 61 to 62, delete "counterions;" and insert --counterions, and are the same or different;--

At Column 19, Claim 1, Line 63, delete "2; and" and insert --2, and are the same or different; and--

At Column 19, Claim 2, Line 65, delete "in" and insert --m--

At Column 20, Claim 6, Lines 58 to 59, delete "counterions;" and insert --counterions, and are the same or different;--

At Column 20, Claim 6, Line 60, delete "2; and" and insert --2, and are the same or different; and--

At Column 22, Claim 17, Lines 29 to 30, delete "counterions;" and insert --counterions, and are the same or different;--

Signed and Sealed this
Twenty-fourth Day of March, 2020

Andrei Iancu
*Director of the United States Patent and Trademark Office*